United States Patent
Yoshimura et al.

(10) Patent No.: US 9,724,051 B2
(45) Date of Patent: Aug. 8, 2017

(54) MEDICAL X-RAY CT PHOTOGRAPHY APPARATUS USING POSITIONAL SHIFT BASED ON ROTATION ANGLE

(71) Applicant: J. MORITA MANUFACTURING CORPORATION, Kyoto-shi, Kyoto (JP)

(72) Inventors: Takahiro Yoshimura, Kyoto (JP); Masakazu Suzuki, Kyoto (JP); Tomoyuki Sadakane, Kyoto (JP)

(73) Assignee: J. MORITA MANUFACTURING CORPORATION, Kyoto-Fu (JP)

( * ) Notice: Subject to any disclaimer, the term of this patent is extended or adjusted under 35 U.S.C. 154(b) by 307 days.

(21) Appl. No.: 14/199,209

(22) Filed: Mar. 6, 2014

(65) Prior Publication Data
US 2014/0254750 A1    Sep. 11, 2014

(30) Foreign Application Priority Data

Mar. 8, 2013   (JP) .................. 2013-046528
Mar. 3, 2014   (JP) .................. 2014-040125

(51) Int. Cl.
*A61B 6/00*   (2006.01)
*A61B 6/03*   (2006.01)
*A61B 6/04*   (2006.01)
*A61B 6/14*   (2006.01)

(52) U.S. Cl.
CPC ............ *A61B 6/0478* (2013.01); *A61B 6/035* (2013.01); *A61B 6/14* (2013.01); *A61B 6/4452* (2013.01); *A61B 6/54* (2013.01)

(58) Field of Classification Search
None
See application file for complete search history.

(56) References Cited

U.S. PATENT DOCUMENTS 3,045,118 A * 7/1962 Hollman .................. A61B 6/14
                                                   378/168
4,125,774 A * 11/1978 Ciavattoni ........... A61B 6/0478
                                                   378/177
(Continued)

FOREIGN PATENT DOCUMENTS

JP    S55-133243 A    10/1980
JP    2004-568 A      1/2004
(Continued)

OTHER PUBLICATIONS

The Office Action from the corresponding Japanese Patent Application No. 2014-040125 issued on Jul. 19, 2016.

*Primary Examiner* — Jason McCormack
*Assistant Examiner* — James Choi
(74) *Attorney, Agent, or Firm* — Shinjyu Global IP

(57) ABSTRACT

A medical X-ray CT photography apparatus body includes a turning arm that supports an X-ray generator and an X-ray detector while the X-ray generator and the X-ray detector are opposed to each other with the subject interposed therebetween, a bracket part that fixedly supports an axial center position of a turning shaft provided in the turning arm, and a support drive part that turns the turning arm about the turning shaft with respect to the bracket part. The medical X-ray CT photography apparatus body also includes a subject chair on which the subject sits, a chair moving mechanism that linearly moves the subject chair in a front-back direction (Y-axis direction) of the subject, and a main-body controller that performs the panoramic X-ray photography by controlling the chair moving mechanism and the support drive part in conjunction with each other.

8 Claims, 9 Drawing Sheets

(56) References Cited

U.S. PATENT DOCUMENTS

| | | | |
|---|---|---|---|
| 4,251,730 A | 2/1981 | Cushman et al. | |
| 4,534,048 A * | 8/1985 | Welander | A61B 6/14 378/38 |
| 7,421,059 B2 | 9/2008 | Suzuki et al. | |
| 2005/0117696 A1 | 6/2005 | Suzuki et al. | |
| 2008/0299511 A1* | 12/2008 | Thoms | A61B 6/04 433/68 |
| 2009/0046835 A1* | 2/2009 | Kodama | A61B 6/035 378/197 |
| 2009/0310845 A1 | 12/2009 | Ogawa et al. | |
| 2010/0246755 A1* | 9/2010 | Suzuki | A61B 6/032 378/11 |
| 2011/0044520 A1 | 2/2011 | Nakai et al. | |
| 2011/0064188 A1* | 3/2011 | Suzuki | A61B 6/14 378/21 |
| 2011/0182402 A1* | 7/2011 | Partain | A61B 6/032 378/9 |
| 2012/0328071 A1* | 12/2012 | Katsumata | A61B 6/14 378/4 |
| 2013/0114799 A1* | 5/2013 | Yamakawa | A61B 6/14 378/207 |

FOREIGN PATENT DOCUMENTS

| | | |
|---|---|---|
| JP | 2007-29168 A | 2/2007 |
| JP | 2010-214023 A | 9/2010 |
| WO | 03/084407 A1 | 10/2003 |
| WO | WO 2009/063974 A1 | 5/2009 |
| WO | 2009/133896 A1 | 11/2009 |

\* cited by examiner

F I G. 2
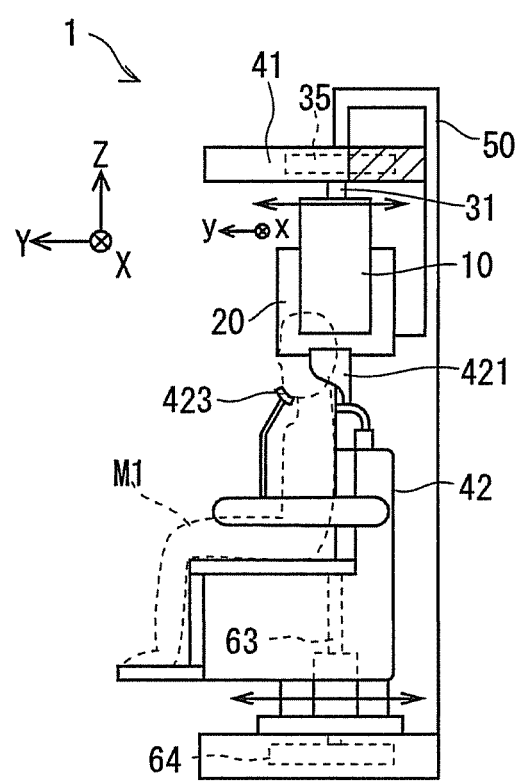

F I G. 7
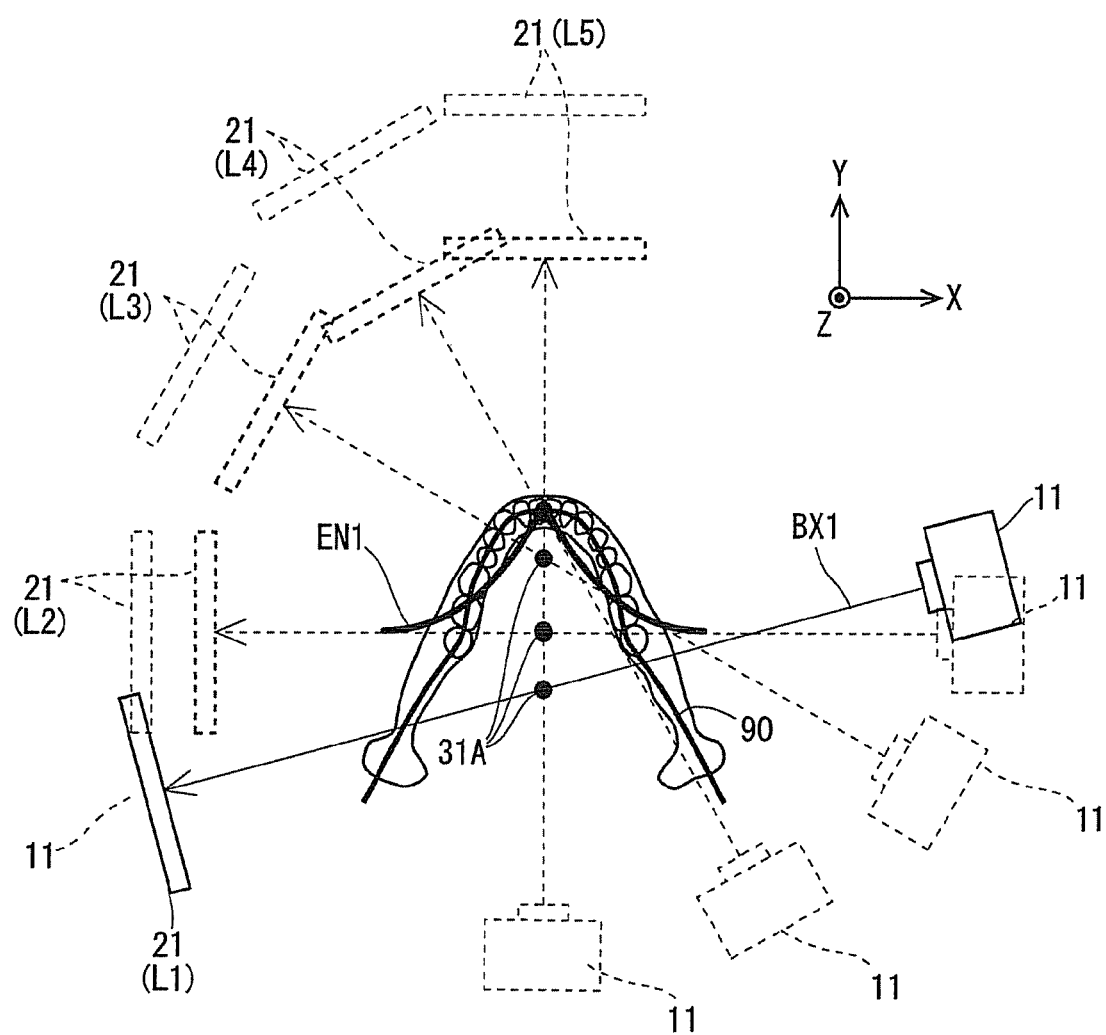

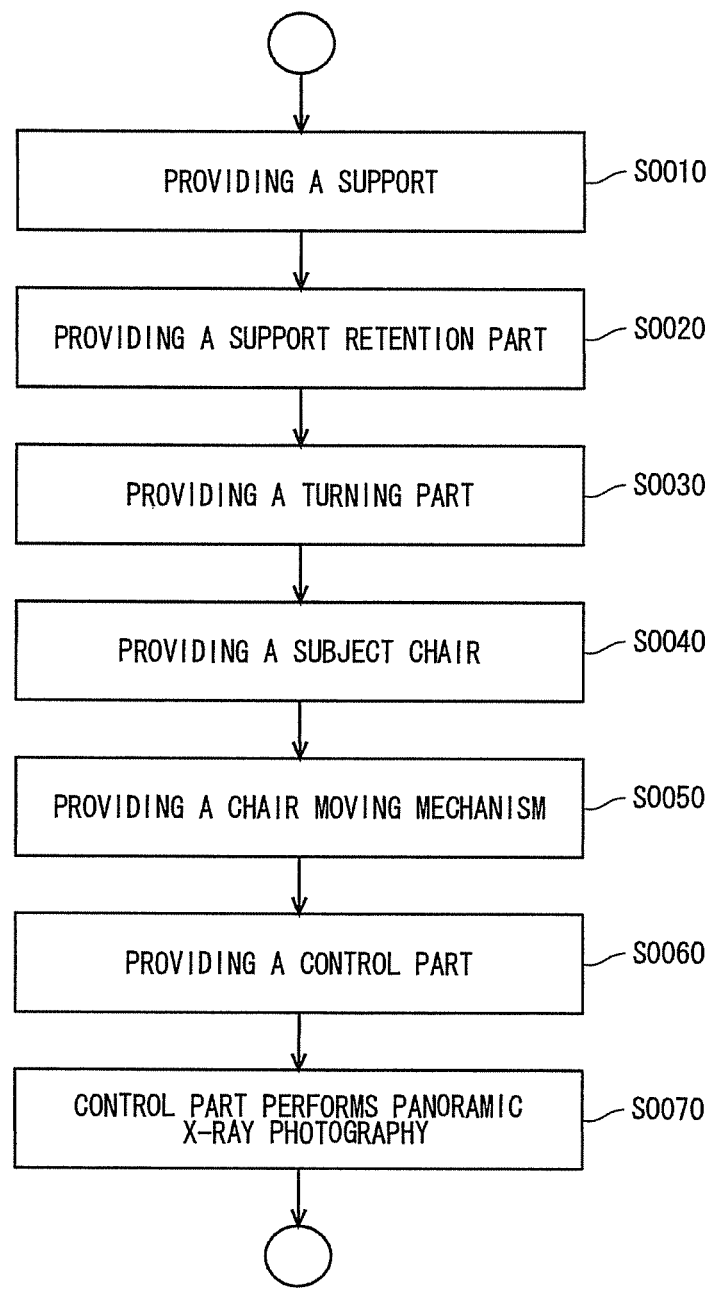

MEDICAL X-RAY CT PHOTOGRAPHY APPARATUS USING POSITIONAL SHIFT BASED ON ROTATION ANGLE

BACKGROUND OF THE INVENTION

Field of the Invention

The present invention relates to a medical X-ray CT photography apparatus.

Description of the Background Art

There is a well known medical X-ray CT photography apparatus in which X-ray CT photography, planar tomography, and curved-surface tomography are performed while an X-ray generator and an X-ray detector are moved relative to a subject interposed therebetween, which sits on and is fixed to a chair (for example, see Japanese Patent Application Laid-Open No. 2004-000568).

However, Japanese Patent Application Laid-Open No. 2004-000568 does not describe the details of panoramic X-ray photography. That is, in the medical X-ray CT photography apparatus including the subject chair, it is unclear how the X-ray generator and the X-ray detector are moved with respect to the subject to perform the panoramic X-ray photography.

SUMMARY OF THE INVENTION

The present invention is directed to a medical X-ray CT photography apparatus.

In accordance with one aspect of the present invention, a medical X-ray CT photography apparatus includes: a support that supports an X-ray generator and an X-ray detector while the X-ray generator and the X-ray detector are opposed to each other with a subject interposed therebetween, the X-ray generator emitting an X-ray beam, the X-ray detector outputting an electric signal according to an intensity of a detected X-ray; a support retention part that journals a turning shaft provided in the support; a turning part that turns the support about the turning shaft with respect to the support retention part; a subject chair on which the subject sits; a chair moving mechanism that linearly moves the subject chair relative to the support in a direction orthogonal to the turning shaft and a front-back direction of the subject; and a control part that performs panoramic X-ray photography by controlling the chair moving mechanism and the turning part in a conjunction way.

According to the medical X-ray CT photography apparatus of the first aspect, the panoramic X-ray photography can be performed well in the medical X-ray CT photography apparatus that performs the X-ray CT photography while the subject sits on the chair.

In accordance with a second aspect of the present invention, in the medical X-ray CT photography apparatus of the first aspect, the chair moving mechanism linearly moves the subject chair with respect to the support turning at a fixed position.

According to the medical X-ray CT photography apparatus of the second aspect, although the subject chair is linearly moved relative to the support that turns in the fixed position, body movement of the subject is hardly generated because the direction of the linear movement is the front-back direction of the subject. Therefore, the panoramic X-ray photography can be performed well while the turning shaft drive mechanism has the simple configuration in which only the support turns.

In accordance with a third aspect of the present invention, in the medical X-ray photography apparatus of the first or second aspect, the control part controls the chair moving mechanism such that the subject chair is moved in a backward direction relative to the support when viewed from the subject who sits on the subject chair at beginning of the panoramic X-ray photography, and then such that the subject chair is moved in a frontward direction relative to the support according to a rotation angle of the support turned by the turning part.

According to the medical X-ray CT photography apparatus of the third aspect, after the subject is relatively moved in the backward direction while the X-ray generator and the X-ray detector are turned about the fixed turning shaft, the subject is relatively moved in the frontward direction to enable the subject to be irradiated with the X-ray from one of the sides of the dental arch to the other side through the anterior tooth side. Therefore, the panoramic X-ray photography can be performed well.

In accordance with a fourth aspect of the present invention, in the medical X-ray CT photography apparatus of third aspect, defining that a horizontal axis is the rotation angle of the support while a vertical axis is a position of the subject chair in the front-back direction relative to the support, a graph of a relationship between the rotation angle and the position during the panoramic X-ray photography includes a parabolic part.

According to the medical X-ray CT photography apparatus of the fourth aspect, the subject can be irradiated with the X-ray for the panoramic X-ray photography according to the dental arch having a horseshoe shape.

In accordance with a fifth aspect of the present invention, the medical X-ray CT photography apparatus of the third or fourth aspect further includes a detector moving mechanism that moves the X-ray detector toward the X-ray generator. In the medical X-ray CT photography apparatus, the control part performs the panoramic X-ray photography by controlling the chair moving mechanism and the detector moving mechanism according to the rotation angle of the support turned by the turning part.

According to the medical X-ray CT photography apparatus of the fifth aspect, a projection scaling factor of an X-ray projection image of the subject projected to the X-ray detector can be adjusted by moving the X-ray detector toward the X-ray generator.

In accordance with a sixth aspect of the present invention, the medical X-ray CT photography apparatus of the third or fourth aspect further includes a detector moving mechanism that brings or pushes the X-ray detector close to or away from the X-ray generator. In the medical X-ray CT photography apparatus, the control part performs the panoramic X-ray photography by controlling the chair moving mechanism and the detector moving mechanism according to the rotation angle of the support turned by the turning part.

According to the medical X-ray CT photography apparatus of the sixth aspect, the projection scaling factor of the X-ray projection image of the subject projected to the X-ray detector can be adjusted by bringing or distancing the X-ray generator close to or away from the X-ray generator.

In accordance with a seventh aspect of the present invention, in the medical X-ray CT photography apparatus of the fifth or sixth aspect, the control part controls the chair moving mechanism and the detector moving mechanism such that the X-ray detector is brought close to the subject when the subject chair is relatively moved in the backward direction, and such that the X-ray detector is pushed away from the subject when the subject chair is relatively moved in the frontward direction.

In accordance with an eighth aspect of the present invention, in the medical X-ray CT photography apparatus of the seventh aspect, the detector moving mechanism moves the X-ray detector with a trajectory in which a ratio of a distance between the X-ray generator and a dental arch of the subject to a distance between the X-ray generator and the X-ray detector becomes substantially constant.

According to the medical X-ray CT photography apparatus of the seventh and eighth aspects, the X-ray detector is moved in conjunction with the relative movement of the subject chair in the front-back direction, which allows the projection scaling factor of the X-ray projection image to be substantially kept constant. Therefore, an arithmetic processing amount necessary to correct the projection scaling factor of the X-ray projection image can be reduced, and image quality of the panoramic photography can be improved.

In accordance with a ninth aspect of the present invention, the medical X-ray CT photography apparatus of the second aspect further includes: a chin rest that supports a lower jaw portion of the subject from at least a side of the frontward direction; and a head rest that supports a back of a head of the subject from at least a side of the backward direction.

According to the medical X-ray CT photography apparatus of the ninth aspect, the subject can firmly be fixed in the front-back direction by the chin rest and the head rest. Therefore, the position of the subject can be stabilized in the front-back direction when the subject is moved in the front-back direction by the chair moving mechanism. Therefore, the panoramic X-ray photography can be performed well.

An object of the present invention is to provide a technology for performing the panoramic X-ray photography well in the medical X-ray CT photography apparatus including the chair on which the subject sits.

These and other objects, features, aspects and advantages of the present invention will become more apparent from the following detailed description of the present invention when taken in conjunction with the accompanying drawings.

BRIEF DESCRIPTION OF THE DRAWINGS

FIG. 2 is a schematic side view of a medical X-ray CT photography apparatus body;

FIG. 7 is a schematic plan view illustrating movement of the X-ray detector during the panoramic X-ray photography in FIG. 4.

FIG. 9 is a flowchart of an example of process of a medical X-ray CT photography apparatus.

DESCRIPTION OF THE PREFERRED EMBODIMENTS

Hereinafter, a preferred embodiment will be described in detail with reference to the drawings. However, the constituent is described in the preferred embodiment only by way of example, but the present invention is not limited to the preferred embodiment.

<1. Preferred Embodiment>
<1.1 Configuration>

Figure 1:
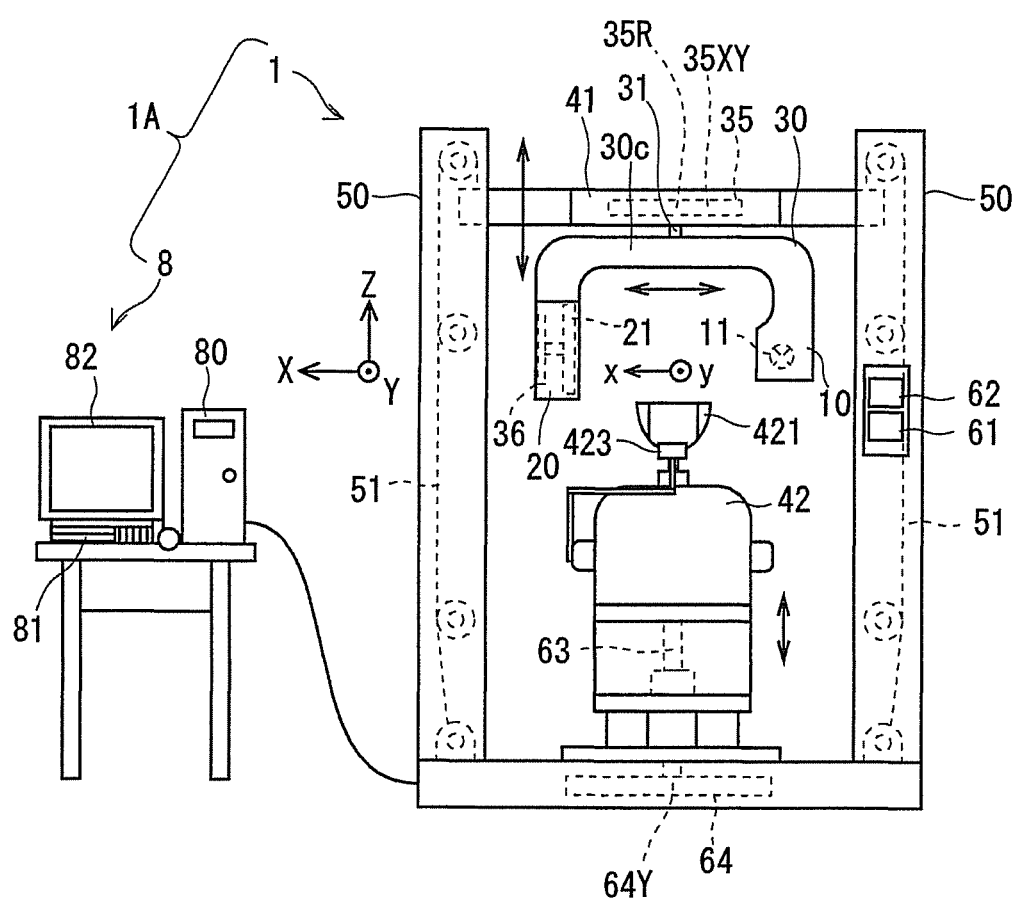
FIG. 1 is a schematic front view of a medical X-ray CT photography apparatus.
Figure 3:
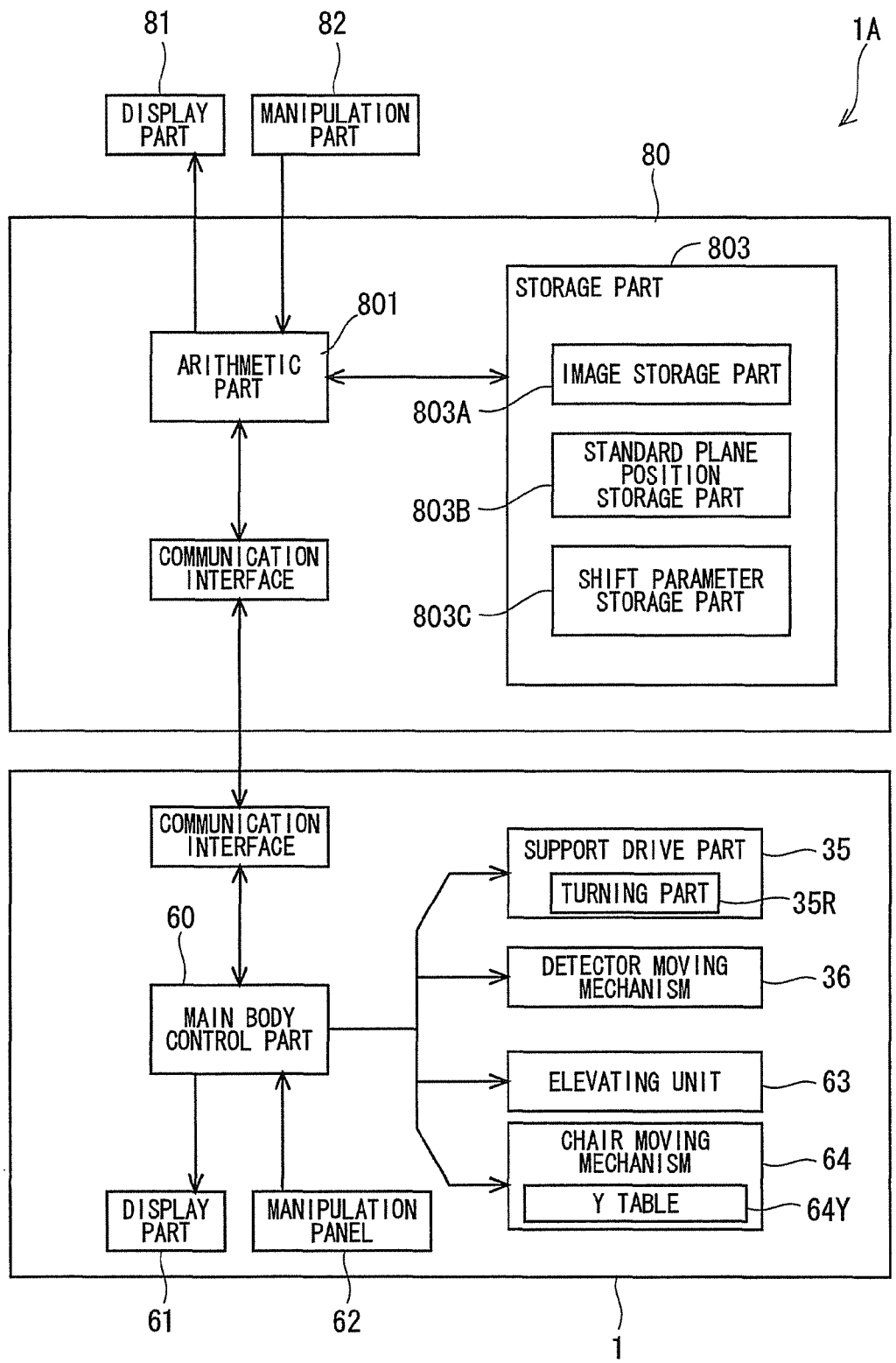
FIG. 3 is a block diagram illustrating a schematic configuration of the medical X-ray CT photography apparatus.

FIG. 1 is a schematic front view of a medical X-ray CT photography apparatus 1A. FIG. 2 is a schematic side view of a medical X-ray CT photography apparatus body 1. FIG. 3 is a block diagram illustrating a schematic configuration of the medical X-ray CT photography apparatus 1A.

The medical X-ray CT photography apparatus 1A includes the medical X-ray CT photography apparatus body 1. As illustrated in FIG. 1, the medical X-ray CT photography apparatus 1A may be configured to include an information processing apparatus 8 in addition to the medical X-ray CT photography apparatus body 1. The medical X-ray CT photography apparatus 1A may be configured to include another constituent.

In the medical X-ray CT photography apparatus body 1, a turning arm 30 (the support) is hung and retained in a central position of a bracket part 41, in which both side end portions are supported by a pair of pillars 50, with a turning shaft 31 interposed between the turning arm 30 and the bracket part 41. That is, the bracket part 41 is the support retention part that supports the turning shaft 31 provided in the turning arm 30, namely, the turning arm 30 is journaled about the central position of the bracket part 41. The turning arm 30 includes tuning parts 30c, to which the X-ray generation part 10 and the X-ray detection part 20 are attached, in both end portions.

The X-ray generation part 10 includes an X-ray generator 11 that is constructed by an X-ray tube and a shielding plate that forms an X-ray emitted from the X-ray generator 11 into an X-ray beam having a predetermined shape. The X-ray detection part 20 includes an X-ray detector 21. The X-ray detector 21 is constructed by a plurality of planarly-arrayed X-ray sensors each of which outputs an electric signal according to an intensity of the detected X-ray. A MOS sensor and a CMOS sensor are suitably used as the X-ray sensor. Any electrically imaging sensor may be used as long as a frame image is obtained. Specifically, another solid-state imaging element including a CCD sensor or a TFT may be used. An image intensifier (I. I.) may be used.

Hereinafter, a direction (in the preferred embodiment, a vertical direction, namely, a vertical direction) parallel to an axial direction of the turning shaft 31 is referred to as a "Z-axis direction", a direction intersecting the Z-axis direction is referred to as an "X-axis direction", and a direction intersecting the X-axis direction and the Z-axis direction is referred to as a "Y-axis direction". The X-axis direction and the Y-axis direction can arbitrarily be defined. In the preferred embodiment, when a test person who is of a subject M1 sits on a subject chair 42 of the medical X-ray CT photography apparatus body 1, a crosswise direction of the test person is defined as the X-axis direction, and a front-back direction of the test person is defined as the Y-axis direction. Particularly, when viewed from the subject M1, a left direction is defined as a −X-direction, a right direction is defined as a +X-direction, a frontward direction is defined as a +Y-direction, and a backward direction is defined as a −Y-direction. When viewed from the subject M1, an upward direction is defined as a +Z-direction, and a downward direction is defined as a −Z-direction. In the preferred embodiment, it is assumed that the X-axis direction, the Y-axis direction, and the Z-axis direction are orthogonal to one another. Hereinafter, sometimes the Z-axis direction is referred to as a vertical direction, and the direction on a plane defined by the X-axis direction and the Y-axis direction is referred to as a horizontal direction.

For the sake of convenience, the direction in which the X-ray generator 11 and the X-ray detector 21 are opposed to each other is referred to as an "x-axis direction". Particularly, the direction from the X-ray generator 11 toward the X-ray detector 21 is referred to as a +x-direction, and the opposite direction is referred to as a −x-direction. The horizontal direction orthogonal to the x-axis direction is referred to as a y-axis direction, the left direction from the X-ray generator 11 toward the X-ray detector 21 is referred to as a +y-direction, and the right direction is referred to as a −y-direction.

Both the side end portions of the bracket part 41 are connected to the belts 51 entrained about pulleys in the pillars 50, a motor is driven to rotate the belt 51, which allows the bracket part 41 to be vertically moved. The turning arm 30 can vertically be elevated according to the vertical movement of the bracket part 41. The elevating mechanism of the turning arm 30 is an example of the support elevating mechanism.

A display part 61 and a manipulation panel 62 are attached to one of the pair of pillars 50 and 50. The display part 61 is constructed by a liquid crystal monitor that displays various pieces of information under the control of a main body control part 60 (see FIG. 3). The manipulation panel 62 is constructed by buttons used to input various commands to the main body control part 60. The manipulation panel 62 is also used, for example, to designate the position of the photographic region of a biological organ.

More specifically, the medical X-ray CT photography apparatus body 1 is configured to be able to perform the panoramic X-ray photography of a jaw portion (including an upper jaw and a lower jaw) of a head in addition to the X-ray CT photography.

The medical X-ray CT photography apparatus body 1 includes the subject chair 42 on which the subject M1 sits. The subject chair 42 fixes the subject M1 in a seated posture. The subject chair 42 is supported by an elevating part 63 from a lower side (−Z-direction side). The subject chair 42 is vertically elevated by driving the elevating part 63.

Alternatively, the subject chair 42 may be eliminated, and the medical X-ray CT photography apparatus body 1 may be configured such that the subject M1 is fixed to a photographing position by a head fixing member in a standing posture. However, the subject M1 can more stably be fixed using the subject chair 42.

The medical X-ray CT photography apparatus body 1 includes a head rest 421 and a chin rest 423. The head rest 421 supports a back of the head of a human body that is of the subject M1 from the back side and both sides, and the chin rest 423 supports the jaw portion of the human body from the front side and the lower side. The head rest 421 and the chin rest 423 are fixed to the subject chair 42. The head rest 421 is configured such that the back of the head of the subject M1 leans thereon to support the back of the head from the back side (the −Y-direction side) and both the sides (the +X-direction side and the −X-direction side). The head rest 421 may support the back of the head of the subject M1 from the lower side (the −Z-direction side). The chin rest 423 is configured such that a front end portion of the lower jaw of the subject M1 is placed thereon, and the chin rest 423 supports the lower jaw portion from the front side (the +Y-direction side) and the lower side (the −Z-direction side).

The turning shaft 31 connected to the turning arm 30 is fixed to a support drive part 35 incorporated in the bracket part 41. The support drive part 35 includes an XY table 35XY constructed by, for example, a motor and a ball screw shaft. The support drive part 35 moves the turning shaft 31 along a horizontal plane (the XY plane) to horizontally move the turning arm 30. The XY table 35XY can linearly move the turning shaft 31 in one direction along the Y-axis direction (that is, the front-back direction viewed from the subject M1).

The support drive part 35 includes a turning part 35R that turns the turning arm 30 with respect to the bracket part 41. In functions of the support drive part 35, when attention is drawn to the function of turning the turning arm 30, the support drive part 35 can be considered as the turning part.

As to a mechanism that turns the turning arm 30, the turning shaft 31 that is of the shaft member is configured to be turnable with respect to the bracket part 41, the turning shaft 31 is fixed to the turning arm 30, and a drive force is transmitted to the turning shaft 31 to turn the turning shaft 31. Alternatively, the turning shaft 31 is fixed turning arm 30, and the drive force is transmitted to the turning arm 30 to turn the turning shaft 31. A turning part 35R that is of an example of the former is constructed by an endless belt wound around the turning shaft 31 and a motor that rotates the endless belt. For example, the support drive part 35 rotates the turning shaft 31 to rotate the turning arm 30 by 360 degrees.

The medical X-ray CT photography apparatus body 1 includes a detector moving mechanism 36. The detector moving mechanism 36 moves the X-ray detector 21 along the x-axis direction. The detector moving mechanism 36 can move the X-ray detector 21 in the −x-direction that is of the direction toward the X-ray generator 11, and in the +x-direction that is of the opposite direction to the −x-direction. For example, the detector moving mechanism 36 of the preferred embodiment is a direct operated mechanism constructed by the motor and the ball screw, and the detector moving mechanism 36 brings or distances the X-ray detector 21 close to or away from the X-ray generator 11. The detector moving mechanism 36 may be constructed by another direct operated mechanism such as a linear motor.

By linearly moving the X-ray detector 21, the X-ray detector 21 can be brought close to or distanced away from the subject M1 (the head) disposed between the X-ray generator 11 and the X-ray detector 21. Therefore, a projection scaling factor, namely, a magnification factor of an X-ray projection image of the subject M1 projected to the X-ray detector 21 can arbitrarily be adjusted.

The subject chair 42 is connected to a chair moving mechanism 64 disposed below the subject chair 42. In the example in FIGS. 1 and 2, the elevating part 63 is placed on the chair moving mechanism 64, and the subject chair 42 is placed on the elevating part 63. Alternatively, the vertical relationship between the chair moving mechanism 64 and the elevating part 63 may be reversed. The chair moving mechanism mechanism 64 and the elevating part 63 may be reversed. The chair moving mechanism 64 includes a Y table 64Y that moves the subject chair 42 in one direction along the Y-axis direction (that is, the front-back direction viewed from the subject M1). As used herein, "the front-back direction of the subject" means the frontward direction (the +Y-direction) and the backward direction (the −Y-direction), which are parallel to a median plane (see FIG. 4) of the subject M1 who sits on the subject chair 42. The subject chair 42 is linearly moved in the Y-axis direction.

The information processing apparatus 8 includes an information processing main body 80 that is of a general computer constructed by a CPU, a ROM, a RAM, and an auxiliary storage device, a display part 81 that is constructed by a liquid crystal monitor, and a manipulation part 82 that is constructed by a mouse or a keyboard. The information processing main body 80 is connected to the medical X-ray CT photography apparatus body 1 through a communication line such as a LAN.

As illustrated in FIG. 3, the information processing main body 80 includes an arithmetic part 801 and a storage part 803. For example, based on the X-ray intensity detected by the X-ray detector 21, the arithmetic part 801 acquires frame data including an X-ray projection image, and processes the frame data to reconstruct various X-ray tomographic images such as a CT image and a panoramic image. The storage part 803 includes an image information storage part 803A in which image information is stored, a standard plane position storage part 803B in which information on a standard plane position is stored, and a shift parameter storage part 803C in which an amount (a shift parameter) relatively moving the turning arm 30 with respect to the subject M1.

Similarly to the manipulation panel 62, various commands may be input to the medical X-ray CT photography apparatus body 1 through the manipulation part 82. In this case, the arithmetic part 801 transmits control information to the main body control part 60 through a communication interface in response to the input, thereby controlling the medical X-ray CT photography apparatus body 1. Specifically, based on the input, the shift parameter is read from the shift parameter storage part 803C according to a type of the X-ray photography such as the panoramic X-ray photography and the X-ray CT photography or a photographing target region, and the shift parameter is transmitted as the control information to the main body control part 60. Therefore, the X-ray photography is properly performed in the medical X-ray CT photography apparatus body 1.

<1. 2 Operation>

An operation of the medical X-ray CT photography apparatus body 1 during the panoramic X-ray photography will be described below.

Figure 4:
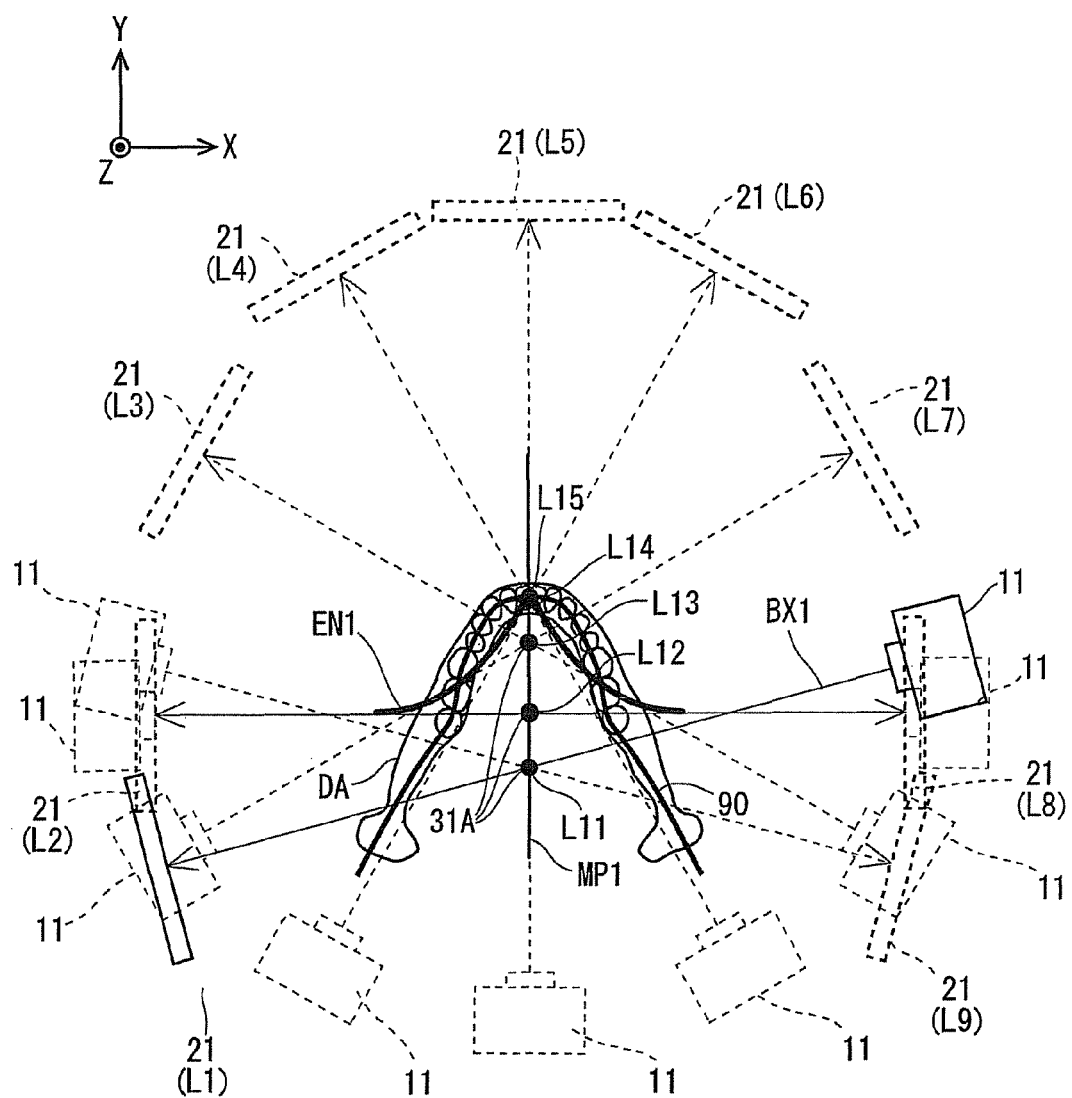
FIG. 4 is a schematic plan view illustrating a positional relationship among an X-ray generator, an X-ray detector, and a subject (a curve of a row of teeth) during panoramic X-ray photography of the medical X-ray CT photography apparatus.

FIG. 4 is a schematic plan view illustrating a positional relationship among the X-ray generator 11, the X-ray detector 21, and the subject M1 (a curve of the row of teeth 90) during the panoramic photography of the medical X-ray CT photography apparatus 1A. In FIG. 4, the curve of the row of teeth 90 indicating a curve of a dental arch DA is illustrated together with the schematic diagram illustrating a lower jaw bone and the plurality of teeth belonging to the lower jaw bone in the subject M1. For example, the curve of the row of teeth 90 can also be set to a shape of a panoramic tomogram that is usually set in the conventional technique. The dental arch DA is a curved locus of the subject, and a curved hard tissue. Because the dental arch DA has a substantial horseshoe shape in a planar view, the curve of the row of teeth 90 is also a curve indicating the substantial horseshoe shape.

Figure 5:
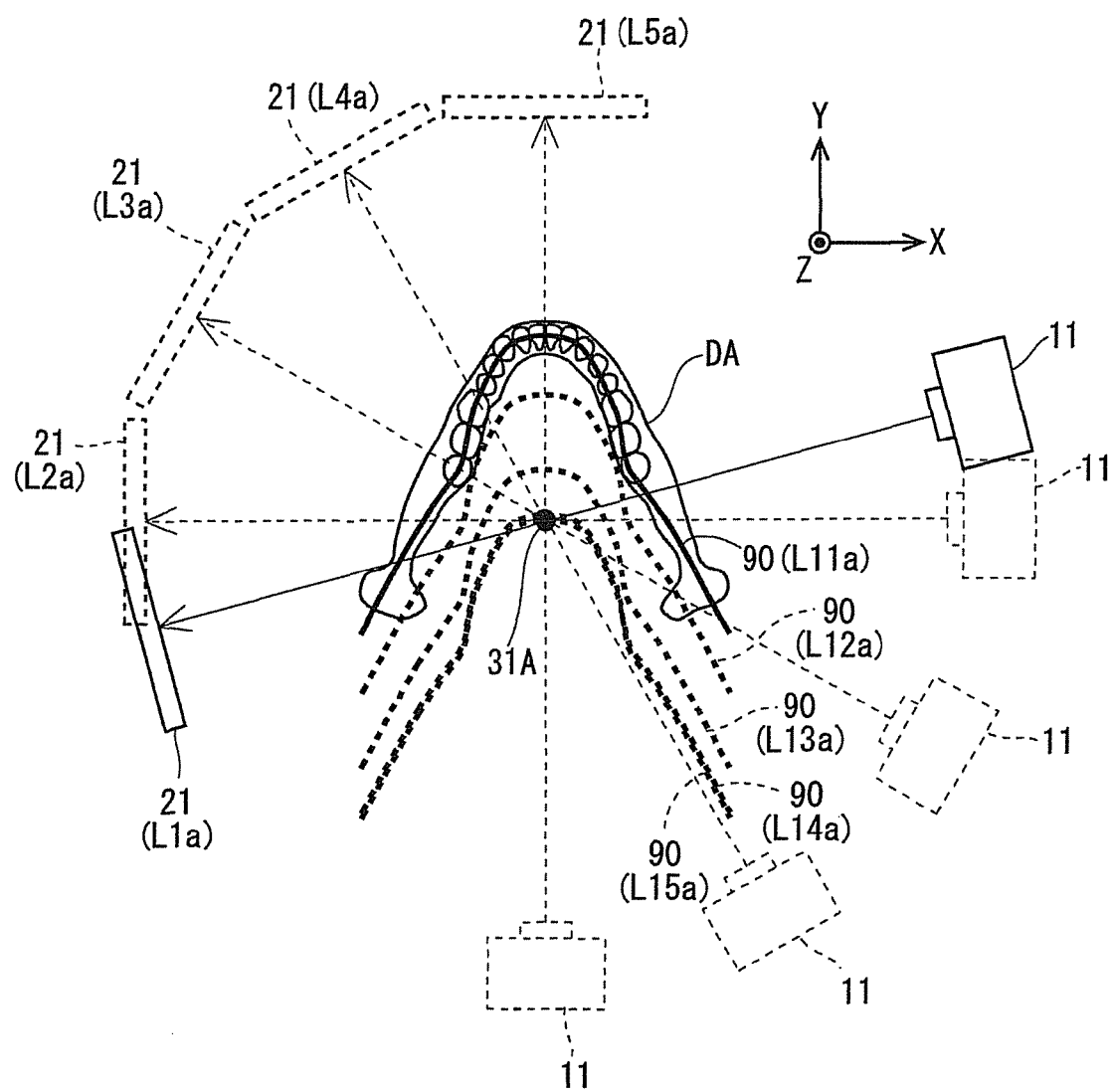
FIG. 5 is a schematic plan view illustrating the positional relationship among the X-ray generator, the X-ray detector, and the subject (the curve of the row of teeth) during panoramic X-ray photography in which a mode is different from that of the panoramic X-ray photography in FIG. 4.

FIG. 5 is a schematic plan view illustrating the positional relationship among the X-ray generator 11, the X-ray detector 21, and the subject M1 (the curve of the row of teeth 90) during the panoramic X-ray photography in which a mode is different from that of the panoramic X-ray photography in FIG. 4. For the sake of convenience, FIG. 5 illustrates the X-ray generator 11 and the curve of the row of teeth 90 when the X-ray detector 21 is located in positions L1 to L5.

A difference between the panoramic X-ray photography in FIG. 4 and the panoramic X-ray photography in FIG. 5 is as follows. In the case that the medical X-ray CT photography apparatus body 1 is viewed from the outside, during the panoramic X-ray photography in FIG. 4, the subject chair 42 does not move, but the turning arm 30 turns while the XY table 35XY moves the turning arm 30 (strictly, a turning center 31A of the turning arm 30) in the Y-axis direction. On the other hand, during the panoramic X-ray photography in FIG. 5, the turning arm 30 turns about the turning center 31A that is of the fixed position, and the subject chair 42 moves in the Y-axis direction.

There is a relative movement relationship between the turning arm 30 and the subject chair 42. For the panoramic X-ray photography in FIG. 4, the turning arm 30 (strictly, the turning center 31A of the turning arm 30 (in the example in FIG. 4, the shaft center of the turning shaft 31)) moves in the Y-axis direction while the subject chair 42 is located in the fixed position. However, the subject chair 42 moves in the Y-axis direction when viewed from the turning arm 30, and the turning arm 30 moves in the Y-axis direction when viewed from the subject chair 42. That is, the turning arm 30 and the subject chair 42 move relatively.

The turning shaft 31 is linearly moved in the Y-axis direction by the XY table 35XY, and the turning shaft 31 moves relatively as described above. Therefore, the support drive part 35 including the XY table 35XY also acts as a chair moving mechanism that linearly moves the subject chair 42 in the Y-axis direction relative to the turning arm 30.

In functions of the support drive part 35, when attention is drawn to the function of linearly moving the turning shaft 31 in the Y-axis direction, the support drive part 35 is the chair moving mechanism that linearly moves the subject chair 42 in the Y-axis direction relative to the turning arm 30. That is, the XY table 35XY can be considered as the chair moving mechanism that linearly moves the subject chair 42 in the Y-axis direction relative to the turning arm 30.

The same holds true for the panoramic X-ray photography in FIG. 5. The subject chair 42 moves in the Y-axis direction while the turning arm 30 (strictly, the turning center 31A of the turning arm 30 (in the example in FIG. 5, the shaft center of the turning shaft 31)) turns in the fixed position. However, the turning arm 30 moves in the Y-axis direction when viewed from the subject chair 42, and the subject chair 42 moves in the Y-axis direction when viewed from the turning arm 30. The turning arm 30 and the subject chair 42 move relatively.

The subject chair 42 is linearly moved in the Y-axis direction by the chair moving mechanism 64 including the Y table 64Y. The subject chair 42 moves relative to the turning arm 30. Therefore, the chair moving mechanism 64 including the Y table 64Y acts as the chair moving mechanism that linearly moves the subject chair 42 in the Y-axis direction relative to the turning arm 30.

In functions of the chair moving mechanism 64, when attention is drawn to the function of linearly moving the subject chair 42 in the Y-axis direction, the chair moving mechanism 64 is the chair moving mechanism that linearly moves the subject chair 42 in the Y-axis direction relative to the turning arm 30. The Y table 64Y can be considered as the chair moving mechanism that linearly moves the subject chair 42 in the Y-axis direction relative to the turning arm 30.

Alternatively, both the turning arm 30 (specifically, the turning center of the turning arm 30) and the subject chair 42 may be moved in the Y-axis direction to perform the relative movement.

In the case that the panoramic X-ray photography is performed as illustrated in FIG. 4, the X-ray generator 11 and the X-ray detector 21 are opposed to each other while the curve of the row of teeth 90DA that is of a part of the subject M1, more specifically the curve of the row of teeth 90 is interposed therebetween. The turning arm 30 turns and moves around the curve of the row of teeth 90. At this point, the X-ray detector 21 turns and moves with respect to the curve of the row of teeth 90 from a position L1 that is of a turning starting position to a position L9 that is of a turning ending position through positions L2 to L8. For example, when the X-ray detector 21 is located in the position L1, the X-ray beam BX1 (X-ray slit beam) is incident to a left rear side portion of the curve of the row of teeth 90. When the X-ray detector 21 is located in the position L5, the X-ray beam BX1 is incident to a central portion (near an anterior tooth) of the dental arch. When the X-ray detector 21 is located in the position L9, the X-ray beam BX1 is incident to a right rear side portion of the curve of the row of teeth 90.

In the panoramic X-ray photography, while the X-ray detector 21 moves from the position L1 to the position L9, the dental arch DA is irradiated with the X-ray beam BX1 such that the X-ray beam BX1 traces the curve of the row of teeth 90. The dental arch DA is irradiated with the X-ray beam BX1 such that the dental arch DA is scanned from the right to the left or from the left to the right, and the X-ray beam BX1 passes through the dental arch DA from a tongue side in each position of the dental arch DA, and is oriented so as to go to a cheek side. At this point, for example, the position of the X-ray generator 11 is controlled such that the X-ray beam BX1 is substantially orthogonal to the row of teeth. When viewed from the subject M1, a trajectory of the X-ray beam BX1 forms an envelope EN1 during the panoramic X-ray photography as illustrated in FIG. 4. The shape of the envelope EN1 depends on the shape of the curve of the row of teeth 90. In the example in FIG. 4, the envelope EN1 is linear symmetry in relation to the median plane MP1 (the plane parallel to the Y-axis direction) of the subject, and the envelope EN1 is a curve, which is curved from +Y-direction side toward the −Y-direction-side while projected onto the +Y-direction side, in a range from the +X-direction side to the median plane MP1.

The row of teeth may be irradiated with the X-ray beam BX1 such that the X-ray beam BX1 is substantially orthogonal to the curve of the row of teeth 90, or the row of teeth may be irradiated with the X-ray beam BX1 such that the X-ray beam BX1 is substantially orthogonal to a curve assumed to be extended along the lower jaw.

For the panoramic X-ray photography in FIG. 4, the subject chair 42 is always fixed to the identical position during the panoramic X-ray photography. According to the rotation angle of the turning arm 30 about the axis of the turning shaft 31, the turning center 31A of the turning arm 30 (in the example in FIG. 4, the shaft center of the turning shaft 31) is driven in the Y-axis direction to move backward and frontward. That is, as the X-ray detector 21 moves from the position L1 to the position L5, the turning center 31A moves in the +Y-direction (the frontward direction for the subject M1) from the position L11 to the position L15 through the positions L12 to L14. When the X-ray detector 21 moves from the position L5 to the position L9, the turning center 31A moves in the −Y-direction (the backward direction for the subject M1) from the position L15 to the position L11.

For the panoramic X-ray photography in FIG. 5, in the medical X-ray CT photography apparatus body 1, during the panoramic X-ray photography, only turning arm 30 is turned by the support drive part 35, and only the subject chair 42 is moved in the Y-axis direction by the chair moving mechanism 64. When viewed from the outside of the medical X-ray CT photography apparatus body 1, the turning arm 30 and the subject chair 42 move as illustrated in FIG. 5.

Specifically, for the panoramic X-ray photography in FIG. 5, turning center 31A of the turning arm 30 (in the example, in FIG. 5, the shaft center of the turning shaft 31) is always fixed to the identical position during the panoramic X-ray photography. According to the rotation angle of the turning arm 30 about the axis of the turning shaft 31, the subject chair 42 is driven in the Y-axis direction to move the curve of the row of teeth 90 backward and frontward in the Y-axis direction. That is, as the X-ray detector 21 moves from the position L1a to the position L5a, the curve of the row of teeth 90 moves in the −Y-direction (the backward direction for the subject M1) from the position L11a to the position L15a through the positions L12a to L14a. When the X-ray detector 21 moves from the position L5a to the position L9a, the curve of the row of teeth 90 moves in the +Y-direction (the frontward direction for the subject M1) from the position L15a to the position L11a. At this point, turning angles of the turning arm 30 in the positions L1a to L9a in FIG. 5 coincide with the turning angles of the turning arm 30 in the positions L1 to L9 in FIG. 4.

The relative movement between the X-ray detector 21 and the subject chair 42 in FIGS. 4 and 5 is as follows. The turning arm 30 starts to turn from the state in which the X-ray detector 21 is located at the position (positions L1 and L1a) on one side with respect to the head of the test person. The X-ray detector 21 moves rotationally around the head, and goes to the position (positions L9 and L9a) on the other side of the head via the front of the head (positions L5 and L5a). During the turning of the turning arm 30, the X-ray generator 11 moved on a locus that becomes the position opposed to the X-ray detector 21 across the head, and the panoramic X-ray photography is performed. While the X-ray detector 21 moves from one side to the front of the head, the subject chair 42 moves relatively in the −Y-direction with respect to the turning arm 30. While the X-ray detector 21 moves from the front of the head to the other side, the subject chair 42 moves relatively in the +Y-direction with respect to the turning arm 30.

The median plane MP1 is a symmetrical plane in the subject indicating bilateral symmetry, and is a plane extending back and forth of the subject. Therefore, using "the median plane MP1", the above description can be restated as follows. While a central portion of the X-ray detection surface of the X-ray detector 21 in a planar view moves from one side of the head to a spot where the central portion intersects the median plane MP1, the subject chair 42 moves relatively in the −Y-direction with respect to the turning arm 30. While the central portion of the X-ray detection surface of the X-ray detector 21 in the planar view moves from the spot where the central portion intersects the median plane MP1 to the other side of the head, the subject chair 42 moves relatively in the +Y-direction with respect to the turning arm 30.

Configuration examples of the support drive part 35 and the chair moving mechanism 64 will be described below. In the example in FIGS. 1 to 3, the support drive part 35 includes the XY table 35XY, and the chair moving mechanism 64 includes the Y table 64Y. The turning center moving mechanism and the subject moving mechanism are not limited to those in FIGS. 1 to 3, but various configuration examples are conceivable. The specific examples are described later.

The XY table 35XY is an example of the turning center moving mechanism that displaces the turning center 31A of the turning arm 30 in the direction intersecting the Z-axis direction when viewed from the outside of the medical X-ray CT photography apparatus body 1. Preferably the direction orthogonal to the Z-axis direction is set to the direction intersecting the Z-axis direction. The XY table 35XY is an XY table on the turning arm side.

The turning center moving mechanism may has any structure as long as the turning center 31A of the turning arm 30 is displaced in the direction intersecting the Z-axis direction. For example, the movement of the turning shaft 31 may be controlled by driving two arms (a first arm AM1 and a second arm AM2) based on a polar coordinate.

Specifically, a fixed turning reference point PT1 is set to the bracket part 41, and one end of the first arm AM1 is journaled in the turning reference point PT1. One end of the second arm AM2 is journaled in the other end of the first arm AM1. The turning shaft 31 is journaled in the other end of the second arm AM2. The first arm AM1 and the second arm AM2 are turned and controlled by arm drive motors, respectively. A turning angle θ2 of the first arm AM1 is controlled with respect to the bracket part 41 and a turning angle θ3 of the second arm AM2 is controlled relative to the first arm AM1, whereby the position of the turning shaft 31 is controlled in a two-dimensional plane perpendicular to the turning shaft 31.

The Y table 64Y is an example of the subject moving mechanism that displaces the subject M1 (strictly, the dental arch DA) in the direction intersecting the Z-axis direction when viewed from the outside of the medical X-ray CT photography apparatus body 1. Preferably the direction orthogonal to the Z-axis direction is set to the direction intersecting the Z-axis direction. The Y table 64Y is a Y table on the chair side.

The subject moving mechanism may have any structure as long as the subject M1 is displaced in the direction intersecting the Z-axis direction. For example, similarly to the turning center moving mechanism, the movement may be controlled by driving the two arms based on the polar coordinate.

The turning center moving mechanism and the subject moving mechanism are not limited to those in FIGS. 1 to 3, but following configuration examples are conceivable.

Main Body Configuration Example 1:

The support drive part 35 includes the turning center moving mechanism, and the chair moving mechanism 64 includes the subject moving mechanism. "The support drive part 35 includes the turning center moving mechanism" includes the case that the support drive part 35 constitutes the turning center moving mechanism, and "the chair moving mechanism 64 includes the subject moving mechanism" includes the case that the chair moving mechanism 64 constitutes the subject moving mechanism.

Main Body Configuration Example 2:

The support drive part 35 includes the turning center moving mechanism but does not include the subject moving mechanism.

Main Body Configuration Example 3:

The support drive part 35 does not include the turning center moving mechanism, but includes only the turning part that turns the turning arm 30. The chair moving mechanism 64 includes the subject moving mechanism.

There is the relative movement relationship between the turning arm 30 and the subject chair 42. That is, both the turning center moving mechanism and the subject moving mechanism are the chair moving mechanism that moves the subject chair 42 relative to the turning arm 30.

Configuration Example 1 of Turning Center Moving Mechanism:

As illustrated in FIGS. 1 to 3, the support drive part 35 includes the turning-arm-side XY table 35XY.

Configuration Example 2 of Turning Center Moving Mechanism:

The support drive part 35 includes a Y table 35Y that displaces the turning center 31A of the turning arm 30 in the Y-axis direction. The support drive part 35 does not include a mechanical element that displaces the turning center 31A of the turning arm 30 in the X-axis direction, but includes the turning-arm-side Y table 35Y.

Configuration Example 1 of Subject Moving Mechanism:

The chair moving mechanism 64 includes an XY table 64XY that can move the subject chair 42 in the Y-axis direction and the X-axis direction. The XY table 64XY is an XY table on the chair side. That is, the chair moving mechanism 64 includes the chair-side XY table 64XY.

Configuration Example 2 of Subject Moving Mechanism:

As illustrated in FIGS. 1 to 3, the chair moving mechanism 64 includes the chair-side Y table 64Y. The mechanical element that displaces the subject chair 42 in the X-axis direction is not included.

The main body configuration example 1 (including both the turning center moving mechanism and the subject moving mechanism) has a high freedom degree of the position control of the turning arm 30 with respect to the subject M1. However, there is a risk of increasing a production cost.

The main body configuration example 2 (including the turning center moving mechanism but not including the subject moving mechanism) and the main body configuration example 3 (not including the turning center moving mechanism but including the subject moving mechanism) have a lower freedom degree of the position control of the turning arm 30 with respect to the subject M1 compared with the main body configuration example 1. However, the production cost can be reduced.

In the case that the configuration example 1 of the turning center moving mechanism is used in the main body configuration example 2 (that is, including the turning-arm-side XY table 35XY but not including the subject moving mechanism), although the turning-arm-side XY table 35XY is included, the panoramic X-ray photography is performed while the turning shaft 31 is moved only in the Y-axis direction as illustrated in FIG. 4. According to the configuration example, for example, when a photographing system including the X-ray generator 11 and the X-ray detector 21 is configured to be able to perform local CT photography in which only a part of the dental arch DA is set to a CT photography region, the turning-arm-side XY table 35XY can be used in the positioning before the CT photography such that the CT photography of the desired local locus is performed using the freedom degree of the two-dimensional movement of the turning shaft 31. In the panoramic X-ray photography, advantageously a burden of controlling the turning arm 30 to be correctly moved can be reduced by controlling the movement of the turning center 31A only in the Y-axis direction.

The turning-arm-side XY table 35XY has the function of displacing the turning center 31A in the X-axis direction in addition to the Y-axis direction, so that at least only the partial regions in the right and left of the dental arch DA can be set to the CT photography region in the local CT photography.

In the case that the configuration example 1 of the subject moving mechanism is used in the main body configuration example 3 (not including the turning center moving mechanism but including the chair-side XY table 64XY), although the chair-side XY table 64XY is included, the panoramic X-ray photography is performed while the subject chair 42 is moved only in the Y-axis direction as illustrated in FIG. 5. Even in the configuration example, for example, when the photographing system is configured to be able to perform the local CT photography, and the chair-side XY table 64XY can be used in the positioning before the CT photography using the freedom degree of the two-dimensional movement of the subject chair 42. In the panoramic X-ray photography, advantageously the burden of controlling the subject chair 42 to be correctly moved can be reduced by controlling the movement of the subject chair 42 only in the Y-axis direction.

The chair-side XY table 64XY has the function of displacing the subject chair 42 in the X-axis direction in addition to the Y-axis direction. Therefore, at least only the partial regions in the right or left of the dental arch DA can be set to the CT photography region in the local CT photography. Particularly, in the configuration, advantageously the body movement is hardly generated when the subject M1 is moved only in the front-back direction.

Additionally, in the configuration, the turning shaft 31 is disposed in the fixed position to turn only the turning arm 30, so that the mechanical structure that drives the turning arm can be simplified to enhance turning accuracy.

In the case that the configuration example 2 of the turning center moving mechanism is used in the main body configuration example 2 (including the turning-arm-side Y table 35Y but not including the subject moving mechanism), and in the case that the configuration example 2 of the subject moving mechanism is used in the main body configuration example 3 (not including the turning center moving mechanism but including the chair-side Y table 64Y), advantageously the production cost can be reduced to the minimum. However, the movement of the subject chair 42 relative to the turning arm 30 is restricted in the X-axis direction. Therefore, for the CT photography, it is conceivable that the CT photographic region is set to a wide region that covers the whole region of the dental arch DA. Alternatively, it is conceivable that the CT photographic region is set to the region that covers the whole front-side or rear-side region of the dental arch DA using the movement of the subject chair 42 in the Y-axis direction relative to the turning arm 30, and that the positioning can be adjusted between the front side and the rear side.

In the case that the XY table 35XY is used as the structure of the mechanism turning the turning arm, for example, as disclosed in Japanese Patent Application Laid-Open No. 2007-29168 applied by the inventor and International Publication No. WO2009/063974, it is conceivable that the turning center 31A of the turning arm 30 is provided in the position different from the shaft center of the turning shaft 31 that is of the mechanical member turning the turning arm 30 about the shaft. However, the moving mechanism can be simplified when the turning center 31A of the turning arm 30 is configured to coincide with the shaft center of the turning shaft 31.

Figure 6A:
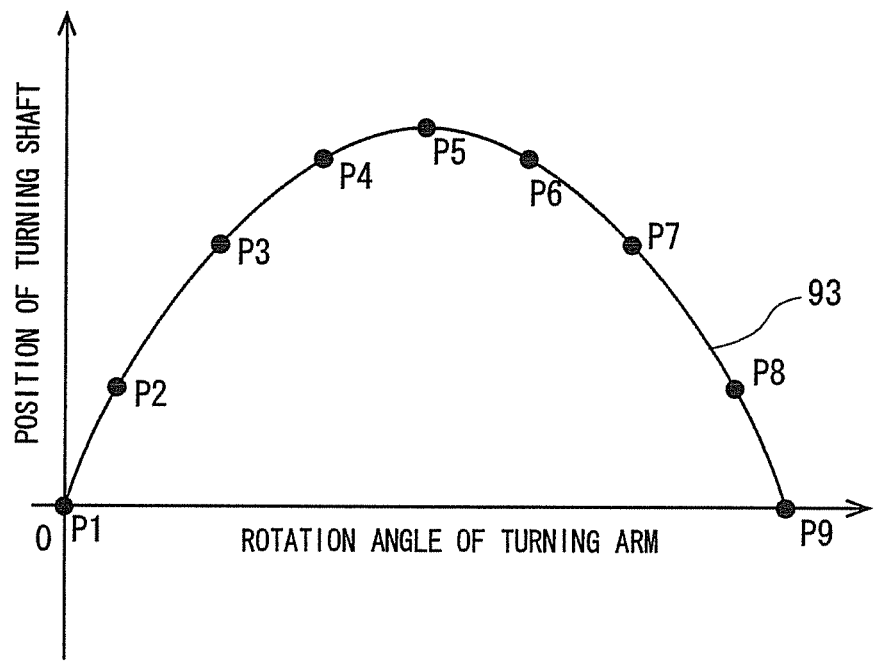
FIGS. 6A and 6B are graphs illustrating a relationship between a rotation angle of a turning arm and a position of a turning shaft or a subject chair.
Figure 6B:
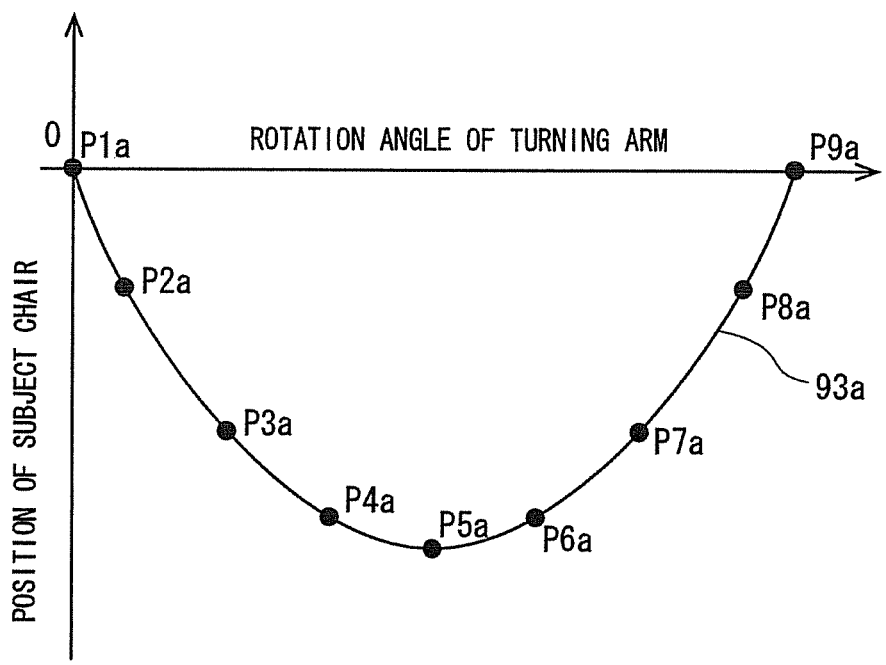

FIGS. 6A and 6B are graphs 93 and 93*a* illustrating a relationship between the rotation angle of the turning arm 30 and the position of the turning shaft 31 and a relationship between the rotation angle of the turning arm 30 and the position of the subject chair 42. FIG. 6A corresponds to the panoramic X-ray photography in FIG. 4, and FIG. 6B corresponds to the panoramic X-ray photography in FIG. 5.

In FIG. 6A, a vertical axis indicates the position of the turning shaft 31 in the Y-axis direction, and a horizontal axis indicates the rotation angle of the turning arm 30. In the vertical axis, a positive side corresponds to the +Y-direction, and a negative side corresponds to the −Y-direction. The change in position of the turning shaft 31 in the Y-axis direction is the change in position of the subject chair 42 in the Y-axis direction relative to the turning arm 30.

In the horizontal axis, the rotation angle is set to zero at the beginning of the turning (that is, when the X-ray detector 21 is located in the position L1). Points P1 to P9 in FIG. 6A correspond to the positions L1 to L9 of the X-ray detector 21, respectively.

For the panoramic X-ray photography in FIG. 4, as illustrated in FIG. 6A, the main body control part 60 controls the support drive part 35 such that the graph 93 illustrating the relationship (a rotation angle/position relationship) between the rotation angle of the turning arm 30 and the position of the turning shaft 31 draws a convex upward parabola. The main body control part 60 controls the turning part 35R and the XY table 35XY of the support drive part 35 such that the turning part 35R and the XY table 35XY work in conjunction with each other. Therefore, in the medical X-ray CT photography apparatus body 1, the panoramic X-ray photography can be performed well according to the curve of the row of teeth 90 having the substantial horseshoe shape.

The shape of the graph 93 illustrating the rotation angle/position relationship is properly changed according to the shape of the curve of the row of teeth 90 as long as the graph 93 includes the convex upward parabola at least partially. The graph 93 does not strictly have the parabolic shape, but may have the substantially parabolic shape.

In FIG. 6B, the vertical axis indicates the position of the subject chair 42 in the Y-axis direction, and the horizontal axis indicates the rotation angle of the turning arm 30. Similarly to FIG. 6A, in the vertical axis, the positive side corresponds to the +Y-direction, and the negative side corresponds to the −Y-direction. The change in position of the subject chair 42 in the Y-axis direction is the change in position of the subject chair 42 in the Y-axis direction relative to the turning arm 30. In the horizontal axis, the rotation angle is set to zero at the beginning of the turning (that is, when the X-ray detector 21 is located in the position L1*a*). Points P1*a* to P9*a* in FIG. 6B correspond to the positions L1*a* to L9*a* of the X-ray detector 21, respectively.

For the panoramic X-ray photography in FIG. 5, as illustrated in FIG. 6B, the main body control part 60 controls the support drive part 35 and the chair moving mechanism 64 while the support drive part 35 and the chair moving mechanism 64 work in conjunction with each other such that the graph 93*a* illustrating the relationship (the rotation angle/position relationship) between the rotation angle of the turning arm 30 and the position of the subject chair 42 draws a convex downward parabola. Therefore, in the medical X-ray CT photography apparatus body 1, the panoramic X-ray photography can be performed well according to the curve of the row of teeth 90 having the substantial horseshoe shape. The shape of the graph 93*s* illustrating the rotation angle/position relationship is properly changed according to the shape of the curve of the row of teeth 90 or X-ray incidence to the curve of the row of teeth 90 as long as the graph 93a includes the convex downward parabola at least partially. The graph 93s does not strictly have the parabolic shape, but may have the substantially parabolic shape.

As described above, according to the medical X-ray CT photography apparatus 1A of the preferred embodiment, the turning shaft 31 or the subject chair 42 is moved in conjunction with the rotation of the turning arm 30, which allows the panoramic X-ray photography to be performed well in addition to the CT photography.

The case that the panoramic X-ray photography is performed to the whole jaw portion including all the teeth is described above by way of example. In the medical X-ray CT photography apparatus body 1, partial panoramic X-ray photography can also be performed. In the partial panoramic X-ray photography, only a part of the jaw including both the lower jaw and the upper jaw, only the lower jaw or the upper jaw, or only a part of the lower jaw or the upper jaw is assigned as the photographic region through the manipulation panel 62, and the X-ray radiation is performed only to the assigned photographic region. Also in this case, the turning shaft 31 is moved in the front-back direction of the subject M1 according to the rotation angle of the turning arm 30 while the turning arm 30 is turned about the turning shaft 31 in the panoramic X-ray photography in FIG. 4, and the subject chair 42 is moved in the front-back direction of the subject M1 according to the rotation angle of the turning arm 30 while the turning arm 30 is turned about the turning shaft 31 in the panoramic X-ray photography in FIG. 5. Therefore, the partial panoramic X-ray photography can be performed.

<Adjustment of Projection Scaling Factor>

In the examples in FIGS. 4 and 5, the distance from the X-ray detector 21 to the portion in which the curve of the row of teeth 90 is irradiated with X-ray beam BX1 fluctuates according to the movements to the positions L1 to L9 and L1a to L9a. In this case, the projection scaling factor of the X-ray projection image acquired in the positions L1 to L9 and L1a to L9a fluctuates. In the case that the projection scaling factor fluctuates, the acquired X-ray projection image is reconstructed by performing arithmetic processing of enlarging or reducing the X-ray projection image to correct the projection scaling factor. Alternatively, the medical X-ray CT photography apparatus body 1 can be configured such that, in order to substantially keep the projection scaling factor constant during the panoramic X-ray photography, the main body control part 60 controls the detector moving mechanism 36 to move the X-ray detector 21 according to the rotation angle of the turning arm 30 turned by the support drive part 35 that is of the turning part. The adjustment of the projection scaling factor will be described with reference to FIGS. 7 and 8.

FIG. 7 is a schematic plan view illustrating the movement of the X-ray detector 21 during the panoramic X-ray photography in FIG. 4. As illustrated in FIG. 7, when the X-ray detector 21 is turned and moved from the position L1 to the position L5 (that is, when the turning center 31A is moved in the frontward direction (the +Y-direction), this means that the subject chair 42 is relatively moved in the backward direction (the −Y-direction)), the detector moving mechanism 36 is controlled such that the X-ray detector 21 comes close to the subject M1 (curve of the row of teeth 90). At this point, the X-ray detector 21 also comes close to the X-ray generator 11.

When the X-ray detector 21 is moved from the position L5 to the position L9 (that is, when the turning center 31A is moved in the backward direction (the −Y-direction)), the detector moving mechanism 36 is controlled such that the X-ray detector 21 is distanced away from the subject M1 (the curve of the row of teeth 90). At this point, the X-ray detector 21 is also distanced away from the X-ray generator 11. When the X-ray detector 21 is located in the positions L6, L7, L8, and L9, the X-ray detector 21 is moved onto the side of the X-ray generator 11 by the movement amount equal to that of the case that the X-ray detector 21 is located in the positions L4, L3, L2, and L1. That is, the movement trajectory of the X-ray detector 21 from the position L1 to the position L9 is bilaterally symmetric in relation to the median plane MP1 of the subject M1. However, the movement trajectory of the X-ray detector 21 is not necessarily bilaterally symmetric, but the movement trajectory may properly be determined according to the shape of the set curve of the row of teeth 90 or the X-ray incidence to the curve of the row of teeth 90.

Thus, the main body control part 60 controls the support drive part 35, the XY table 35XY, and the detector moving mechanism 36 according to the rotation angle of the turning arm 30 turned by the turning part 35R, and performs the panoramic X-ray photography.

In FIG. 7, the X-ray detector 21 can move in the +x-direction and the −x-direction toward the X-ray generator 11. A focal point that is of a spot where energy is generated as the X-ray exists in an X-ray generation source such as an X-ray tube of the X-ray generator 11. The X-ray detector 21 can move in the +x-direction and the −x-direction along the direction connecting the X-ray generator 11 and the turning shaft 31, particularly the direction connecting a focal position of the X-ray generator 11 and the shaft center of the turning shaft 31.

For the panoramic X-ray photography in FIG. 5, the movement amount of the X-ray detector 21 is equal to that of the panoramic X-ray photography in FIG. 4. That is, the displacement amount of the X-ray detector 21 in the +x-direction and the −x-direction with respect to the X-ray generator 11 in the case that the X-ray detector 21 is turned and moved from the position L1a to the position L9a corresponds to the displacement amount of the X-ray detector 21 in the +x-direction and the −x-direction with respect to the X-ray generator 11 in the case that the X-ray detector 21 is turned and moved from the position L1 to the position L9 during the panoramic X-ray photography in FIG. 4.

Thus, the main body control part 60 controls the chair moving mechanism 64, the Y table 64Y, and the detector moving mechanism 36 according to the rotation angle of the turning arm 30 turned by the turning part 35R, and performs the panoramic X-ray photography.

Figure 8:
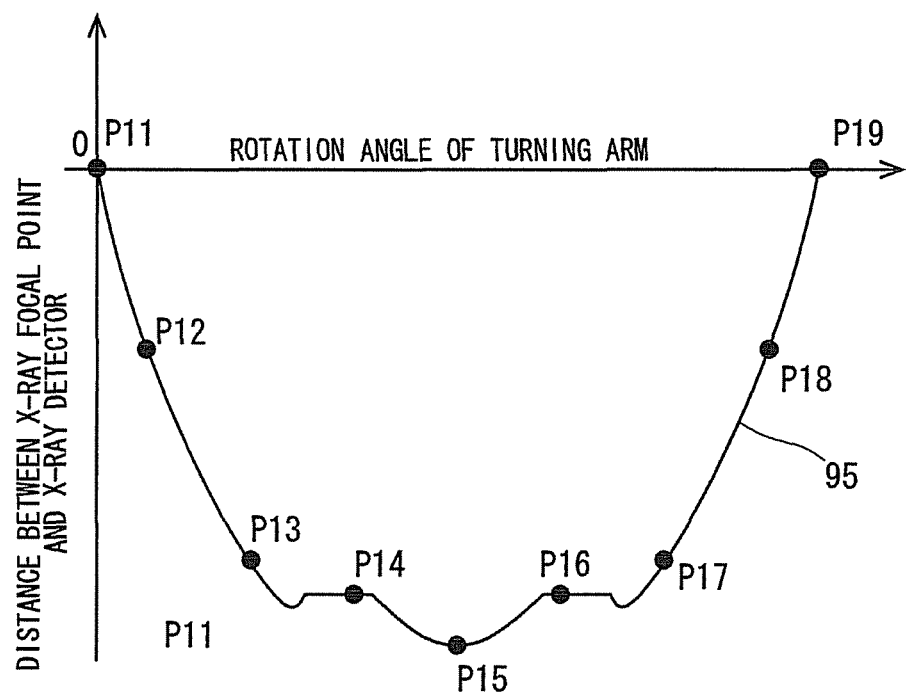
FIG. 8 is a graph illustrating a relationship between the rotation angle of the turning arm and a distance from a focal position of an X-ray beam to a X-ray detection surface of the X-ray detector during the panoramic X-ray photography in FIGS. 4 and 5.

FIG. 8 is a graph 95 illustrating a relationship between the rotation angle of the turning arm 30 and the distance from the focal position of the X-ray beam BX1 to the X-ray detection surface of the X-ray detector 21 during the panoramic X-ray photography in FIGS. 4 and 5. In FIG. 8, the vertical axis indicates the distance from the focal position of the X-ray beam BX1 to the X-ray detection surface, and the horizontal axis indicates the rotation angle of the turning arm 30. In the vertical axis, the movement amount is set to zero in the positions L1 and L1a. Points P11 to P19 in FIG. 8 correspond to the positions L1 to L9 and L1a to L9a of the X-ray detector 21, respectively.

As illustrated in FIG. 8, the graph 95 illustrating the relationship (the rotation angle—distance relationship) between the rotation angle of the turning arm 30 and the distance from the focal position to the X-ray detection surface is a substantially convex downward parabola. The X-ray detector 21 separates farthest away from the X-ray generator 11 when the X-ray detector 21 is located in the position L1 or the position L9, and the X-ray detector 21 comes closest to the X-ray generator 11 when the X-ray detector 21 is located in the position L5.

In the preferred embodiment, an incident angle of the X-ray beam BX1 to each portion of the curve of the row of teeth 90 is set so as to be equal to an incident angle of the conventional panoramic X-ray photography. The displacement caused by the separation and approximation of the X-ray detector 21 with respect to the X-ray generator 11 is set such that a ratio of the distance between the focal position and the X-ray detection surface to the distance between the curve of the row of teeth 90 and the X-ray detection surface is substantially kept constant. As a result, the relationship between the rotation angle of the turning arm 30 and the distance from the focal position to the X-ray detection surface is expressed by the substantially convex downward parabola as illustrated by the graph 95 in FIG. 8. The shape of the graph 95 of the rotation angle-distance relationship is determined according to the shape of the set curve of the row of teeth 90.

As illustrated in FIGS. 7 and 8, the position of the X-ray detector 21 is controlled according to the rotation angle of the turning arm 30 such that the ratio of the distance between the X-ray generator 11 and the dental arch DA to the distance between the X-ray generator 11 and the X-ray detector 21 is substantially kept constant, more specifically such that the ratio of the distance between the focal position and the curve of the row of teeth 90 to the distance between the focal position and the X-ray detection surface is substantially kept constant, whereby the projection scaling factor of each X-ray projection image of the subject M1 projected to the X-ray detector 21 can substantially be kept constant. Therefore, the arithmetic processing amount can be reduced in the processing of correcting the scaling factor of the X-ray projection image in the information processing apparatus 8. The X-ray projection image is reconstructed without correcting the obtained X-ray projection image, which allows the improvement of the image quality in the panoramic X-ray photography.

2. <Modifications>

Although the preferred embodiment is described above, the present invention is not limited to the preferred embodiment, but various modifications can be made.

For example, in the medical X-ray CT photography apparatus body 1, the head of the subject M1 is fixed by the head rest 421 and the chin rest 423. Alternatively, the head of the subject M1 may be fixed by an ear rod that is inserted in an ear canal of the subject M1 to regulate the position of the ear canal.

The medical X-ray CT photography apparatus body 1 has the bridge structure in which both the end portions of the bracket part 41 are supported by the pair of pillars 50. Alternatively, like the conventional panoramic X-ray photography apparatus, the bracket part 41 is supported by only one pillar, and the cost reduction may be achieved by the simple structure.

In the medical X-ray CT photography apparatus body 1, the projection scaling factor is adjusted by bringing or distancing the X-ray detector 21 close to or away from the X-ray generator 11. Alternatively, the X-ray detector 21 may be brought close to or distanced away from the subject M1 by horizontally moving the whole of the turning arm 30. Therefore, the projection scaling factor can be adjusted. In the turning arm 30, the portion (tuning part 30c) connecting the X-ray generation part 10 and the X-ray detection part 20 is configured to be stretchable, and the X-ray detector 21 may be brought close to or distanced away from the X-ray generator 11 by stretching the portion.

As described above, the support drive part 35 of the medical X-ray CT photography apparatus body 1 moves the turning arm 30 in the X-axis direction and the Y-axis direction. However, because the chair moving mechanism 64 can move the subject chair 42 in the Y-axis direction, the moving mechanism of the Y-axis direction may be eliminated from the support drive part 35.

The chair moving mechanism 64 of the medical X-ray CT photography apparatus body 1 may move the subject chair 42 only in the Y-axis direction, or the subject chair 42 may also be moved in the X-axis direction by providing the chair-side XY table. In this case, the mechanism that moves the turning arm 30 in the X-axis direction can be eliminated from the support drive part 35. The mechanism that turns the turning arm 30 relative to the subject M1 may be provided on the side of the turning arm 30, and the moving mechanism that moves the subject M1 in the direction orthogonal to turning shaft 31 relative to the turning arm 30 may be provided on the side of the subject M1, whereby the apparatus cost can be reduced while the apparatus configuration is simplified.

One of the support elevating mechanism in which the pulley and the belt 51 are used and the elevating part 63 that elevates the subject chair 42 may be eliminated.

FIG. 9 shows an example of process of a medical X-ray CT photography apparatus which can be applied to the above mentioned embodiment. The process includes the following Steps S0010 to S0060 for providing a medical X-ray CT photography apparatus 1A. The order of Steps S0010 to S0060 can be changed.

In Step S0010, there is provided a support 30 that supports an X-ray generator 11 and an X-ray detector 21 in a condition that the support 30 that supports the X-ray generator 11 and the X-ray detector 21 while the X-ray generator 11 and the X-ray detector 21 are opposed to each other with a subject M1 interposed therebetween in X-ray photography. The X-ray generator 11 emits an X-ray beam. The X-ray detector 21 outputs an electric signal according to an intensity of a detected X-ray.

In Step S0020, there is provided a support retention part 41 that journals a turning shaft 31 provided in the support 30.

In Step S0030, there is provided a turning part 35R that turns the support 30 about the turning shaft 31 with respect to the support retention part 41.

In Step S0040, there is provided a subject chair 42 on which the subject M1 sits.

In Step S0050, there is provided a chair moving mechanism 64 that linearly moves the subject chair 42 relative to the support 30 in a direction orthogonal to the turning shaft 31 and a front-back direction of the subject M1.

In Step S0060, there is provided a control part 60.

The process contains a controlling step S0070 as following.

In Step S0070, the control part 60 performs panoramic X-ray photography by controlling the chair moving mechanism 64 and the turning part 35R in a conjunction way.

Here, the panoramic X-ray photography described with FIG. 4 or FIG. 5 is an example of the panoramic X-ray photography controlling the chair moving mechanism 64 and the turning part 35R in the conjunction way.

While the invention has been shown and described in detail, the foregoing description is in all aspects illustrative and not restrictive. It is therefore understood that numerous modifications and variations can be devised without departing from the scope of the invention.

What is claimed is:

1. A medical X-ray CT photography apparatus comprising:
   a support that supports an X-ray generator and an X-ray detector while the X-ray generator and the X-ray detector are opposed to each other with a subject interposed therebetween, the X-ray generator emitting an X-ray beam, the X-ray detector outputting an electric signal according to an intensity of a detected X-ray;
   a support retention part that journals a turning shaft provided in the support;
   a turning part that turns the support about the turning shaft with respect to the support retention part;
   a subject chair on which the subject sits;
   a chair moving mechanism that moves the subject chair relative to the support in at least a direction orthogonal to the turning shaft and a front-back direction of the subject; and
   a circuit that performs panoramic X-ray photography by controlling the chair moving mechanism and the turning part in conjunction with each other;
   a position of the turning shaft and a position of the support retention part are generally fixed relative to each other;
   in a local CT photography in which only a part of the subject is set as a CT photography area, the chair moving mechanism moving the subject chair such that the subject is positioned for the local CT photography prior to the local CT photography;
   in the panoramic X-ray photography, the turning part turns and moves the support so as to turn and move the X-ray generator from one side of a head of the subject to an opposite side of the head via a front of the head;
   the circuit controlling the chair moving mechanism in response to the turning angle of the support when the panoramic X-ray photography is performed, such that:
   the subject chair is moved linearly in a backward direction relative to the support while the X-ray detector goes from the opposite side of the head to the front of the head;
   the subject chair is moved linearly in a frontward direction relative to the support while the X-ray detector goes from the front of the head to the opposite side of the head;
   the chair moving mechanism linearly moving the subject chair with respect to the support turning at a fixed position; and
   defining that a horizontal axis is a rotation angle of the support while a vertical axis is a position of the subject chair in the front-back direction relative to the support, and a graph of a relationship between the rotation angle and the position during the panoramic X-ray photography includes a parabolic part.

2. The medical X-ray CT photography apparatus according to claim 1, further comprising:
   a chin rest that supports a lower jaw portion of the subject from at least a side of the frontward direction; and
   a head rest that supports a back of a head of the subject from at least a side of the backward direction.

3. The medical X-ray CT photography apparatus according to claim 1, the circuit controls the chair moving mechanism and the turning part such that during the panoramic X-ray photography, a trajectory of the X-ray beam, which is applied to a dental arch of the subject, forms an envelope.

4. A medical X-ray CT photography apparatus comprising:
   a support that supports an X-ray generator and an X-ray detector while the X-ray generator and the X-ray detector are opposed to each other with a subject interposed therebetween, the X-ray generator emitting an X-ray beam, the X-ray detector outputting an electric signal according to an intensity of a detected X-ray;
   a support retention part that journals a turning shaft provided in the support;
   a turning part that turns the support about the turning shaft with respect to the support retention part;
   a subject chair on which the subject sits;
   a chair moving mechanism that moves the subject chair relative to the support in at least a direction orthogonal to the turning shaft and a front-back direction of the subject;
   a circuit that performs panoramic X-ray photography by controlling the chair moving mechanism and the turning part in conjunction with each other; and
   a detector moving mechanism that moves the X-ray detector along a direction between the X-ray detector and the X-ray generator relative to the support, wherein a distance between the X-ray detector and the X-ray generator is increased or decreased; and wherein
   in the panoramic X-ray photography, the turning part turns and moves the support so as to turn and move the X-ray generator from one side of a head of the subject to an opposite side of the head via a front of the head,
   the circuit controlling the chair moving mechanism and the detector moving mechanism in response to the turning angle of the support when the panoramic X-ray photography is performed, such that:
   the subject chair is moved linearly in a backward direction relative to the support while the X-ray detector goes from the one side of the head to the front of the head;
   the subject chair is moved linearly in a frontward direction relative to the support while the X-ray detector goes from the front of the head to the opposite side of the head;
   the X-ray detector is moved toward or away from the X-ray generator while the subject chair is moved relatively backward or forward;
   the chair moving mechanism linearly moving the subject chair with respect to the support turning at a fixed position; and
   defining that a horizontal axis is a rotation angle of the support while a vertical axis is a position of the subject chair in the front-back direction relative to the support, and a graph of a relationship between the rotation angle and the position during the panoramic X-ray photography includes a parabolic part.

5. The medical X-ray CT photography apparatus according to claim 4, wherein the X-ray detector is moved toward or away from the X-ray generator while the subject chair is moved relatively backward and forward.

6. The medical X-ray CT photography apparatus according to claim 4 wherein,
   the X-ray detector is moved toward the X-ray generator while the subject chair is moved relatively backward and the X-ray detector is moved away from the X-ray generator while the subject chair is moved relatively forward.

7. The medical X-ray CT photography apparatus according to claim 5, wherein,
   the detector moving mechanism moving the X-ray detector with a trajectory in which a ratio of a distance between the X-ray generator and a dental arch of the subject to a distance between the X-ray generator and the X-ray detector becomes substantially constant.

8. The medical X-ray CT photography apparatus according to claim 6 wherein,
the detector moving mechanism moving the X-ray detector with a trajectory in which a ratio of a distance between the X-ray generator and a dental arch of the subject to a distance between the X-ray generator and the X-ray detector becomes substantially constant.

* * * * *